United States Patent [19]

Falla

[11] 4,122,947

[45] Oct. 31, 1978

[54] PRE-PACKAGED PATIENT IDENTIFICATION KIT

[76] Inventor: Marjorie B. Falla, 3056 California St., Oakland, Calif. 94602

[21] Appl. No.: 873,008

[22] Filed: Jan. 27, 1978

[51] Int. Cl.[2] .......... A61B 19/02

[52] U.S. Cl. .......... 206/569; 40/2 R; 128/2 R

[58] Field of Search .......... 206/569, 568, 572, 223; 128/2 R, DIG. 5

[56] References Cited

U.S. PATENT DOCUMENTS

| | | | |
|---|---|---|---|
| 2,561,894 | 7/1951 | Wallich | 40/2 R |
| 3,266,298 | 8/1966 | Whitehad | 40/2 R |
| 3,272,319 | 9/1966 | Brewer | 206/569 |
| 3,526,125 | 9/1970 | Gilford | 128/2 R |
| 3,593,443 | 7/1971 | Demetrius | 40/2 R |
| 3,650,393 | 3/1972 | Reiss | 206/569 |
| 3,771,717 | 11/1973 | McDermott | 128/2 R |
| 3,814,049 | 6/1974 | Hunter | 128/2 R |
| 3,917,456 | 11/1975 | Eckstein | 206/569 |

*Primary Examiner*—Herbert F. Ross
*Attorney, Agent, or Firm*—Warren, Chickering & Grunewald

[57] ABSTRACT

A pre-packaged patient identification kit and method for assuring correlation between a patient, his specimens and his records is disclosed. The kit is preferably formed as a transparent package inside of which a wristband, at least one specimen container and, optionally, a label are disposed. The wristband, specimen container, and label are pre-numbered with identical patient identifying indicia. The kit is used by first visually verifying that all indicia are identical, attaching the wristband to the patient, taking a specimen from the patient and placing it in the specimen container, and placing the label means on the patient's record. After analysis of the specimen, the patient identifying indicia is copied onto a label for a therapeutic agent to be given to the patient; and finally, before administration of the therapeutic agent to the patient, the indicia on the label of the therapeutic agent is checked against the indicia on the patient's wristband and his records.

11 Claims, 3 Drawing Figures

PRE-PACKAGED PATIENT IDENTIFICATION KIT

BACKGROUND OF THE INVENTION

In addition to the many and varied medical problems which hospitals are called upon to treat, they also face a serious procedural or administrative problem which affects the medical treatment of patients, namely, the correlation of patients to specimens, records and thus diagnosis and treatment. Perhaps this problem is nowhere more acutely felt than in connection with blood transfusions. As is stated in TRANSFUSION, the Official Journal of the American Association of Blood Banks, "Once the decision to transfuse —rightly or wrongly, has been made, there is a very serious risk of identification errors. Indeed, human mistakes, particularly in identifying blood samples and patients, continue to cause the largest proportion of transfusion fatalities." (July-August, 1977, at page 305)

The problem of assuring correlation between a patient, his blood specimen and the blood unit from the blood bank is particularly troublesome in hospitals in urban areas which act as major trauma centers and may be called upon to treat several acutely hemorrhaging patients at the same time. The need for blood components on a STAT basis is common, and may be complicated by the fact that the patient's identify is often unknown. Clerical errors in the handling of specimens under the pressure of emergency service understandably can occur, and they are extremely dangerous since the patient is often taken directly from the emergency room to the operating room in an anesthetized condition, making the infusion of mis-matched blood more likely to be lethal.

While the problem is perhaps most dramatically illustrated in connection with correlating the blood specimens taken from a patient with the blood components to be infused into the patient, the same potential problem arises in connection with correlating other types of specimens and pharmacological agents, as well as patient records and treatment. Clerical error can result in the dispensing of the right medicine or treatment to the wrong patient, with disastrous consequences.

Some attempts have been made in connection with blood transfusions to help the physicians, phlebotomists, and technologists assure the correlation of blood specimens, units of blood and the patient by use of a separate and additional identifying means. One such prior system is known as the TYPENEX System, which is a kit marketed by Fenwal Laboratories of Deerfield, Illinois. The TYPENEX System includes a package of ten wristbands and ten strips of pre-numbered labels each having identical indicia or numbers thereon. The wristbands further have a label on which the patient's name can be entered removably positioned thereon. The system is used by writing the name, hospital identification number and the date on the label on the wristband, usually by copying from the hospital wristband. This label is then removed and pressed onto a blood specimen tube, carrying with it a patient identifying indicia. The information recorded on this label is also automatically transferred through to a portion of the wristband under the removable label. Additionally, a strip of labels having the identifying indicia on the wristband is also attached to the specimen tube so that they will travel with the tube to the blood bank area. The labels in the strip can then be detached and placed upon the units of blood that are matched to the patient specimen.

While advantageous in many respects over the prior systems, the TYPENEX System inherently has certain disadvantages. First, while the carbon imprint of the patient's number remains on the wristband, the labels can be peeled off by the patients, either deliberately or unconsciously and can become affixed to something else. Secondly, when there are multiple patients, multiple wristbands, multiple strips of labels and multiple specimen tubes, making wristband entries, placing the proper labels on the proper sample tubes, and generally locating the parts for and "building" the specimen tube-patient correlation system under the pandemonium of emergency trauma center conditions is not highly reliable. The writing, peeling off and sticking on of labels will be the first procedures eliminated in emergency conditions by physicians trying to get to the treatment of patients. Still further, the strip of labels which are removably attached to the blood specimen tubes can interfere with such blood bank activities as centrifuging. Some would have to be removed and a further responsibility placed on the technologist to properly use and/or destroy them.

A similar system is marketed under the trademark IDENT-A-BLOOD by Hollister Incorporated of Chicago, Illinois. The IDENT-A-BLOOD system includes a wristband and a sheet of pressure sensitive labels. The sheet of labels includes a wristband label, a specimen tube label, a plurality of chart, blood bank charge and identification labels, chart and log book labels, and patient, physician and hospital identification labels. Again, the system is based upon the physician's or other phlebotomist's ability to "build" the system under emergency conditions. The wristband label has to be filled in, peeled off the master label sheet and inserted into the wristband, all before mounting the wristband on the patient. The insertion process alone can be tedious or impossible if the wristband tube is not completely open, which does occur. The sample label has to be peeled off the master sheet and placed on the specimen tube, and the master sheet has to be forwarded to the blood bank with the specimen so that still another label can be peeled off and placed on the unit of blood to be returned to the patient. Additionally, chart labels and the like have to be peeled off and placed on appropriate records for the patient.

The prior multiple label patient-specimen correlation assurance systems, therefore, can be seen to have two inherent disadvantages. First, the necessity of building up the system under emergency conditions may produce an error in labeling or the like; and secondly, the complexity and time required to build up the correlation apparatus may cause physicians, phlebotomists and technicians to simply relegate use of the system to those situations in which time is not critical.

SUMMARY OF THE INVENTION

A. Objects of the Invention

Accordingly, it is an object of the present invention to provide a pre-packaged patient identification kit and method for use in assuring correlation between a patient and his specimens during diagnosis and treatment of the patient, which system is ready for use without the need for the creation or building of the system under emergency or routine conditions.

It is a further object of the present invention to provide a pre-packaged patient identification kit and method which is easier and requires less time to use and enhances the correlation between patients, specimens and patient records.

Still a further object of the present invention is to provide a pre-packaged patient identification kit and method which is inexpensive to manufacture, can be used with a minimum of instruction, and affords improved safety for the patient against clerical errors.

Another object of the present invention is to provide a pre-packaged patient identification kit and method which can be used to improve the correlation between a patient and all phases of his in-hospital treatment including laboratory, pharmacy, blood bank, records and physician services.

The pre-packaged patient identification kit and method of the present invention have other objects and features of advantage which will become apparent from or are set forth in more detail in the following specification and accompanying drawing.

B. Brief Summary

The pre-packaged patient identification kit of the present invention is comprised, briefly, of package means, wristband means provided with a patient identifying indicia previously affixed thereto in a tamper-resistant manner, at least one specimen container means provided with an identical patient identifying indicia previously affixed thereto in a tamper-resistant manner, with the wristband means and specimen container means being removably positioned in the package means. Optionally, the package means may be transparent, and the kit can further include label means formed for attachment to a record of the patient and having patient identifying indicia thereon. The wristband means, specimen container means and label means all are positioned in the package means for visual verification of the identical nature of the patient identifying indicia.

The method of the present invention is comprised of the improvement of providing the specimen container means along with the wristband means as a kit with each being pre-numbered with identical patient identifying indicia.

Figure 1:
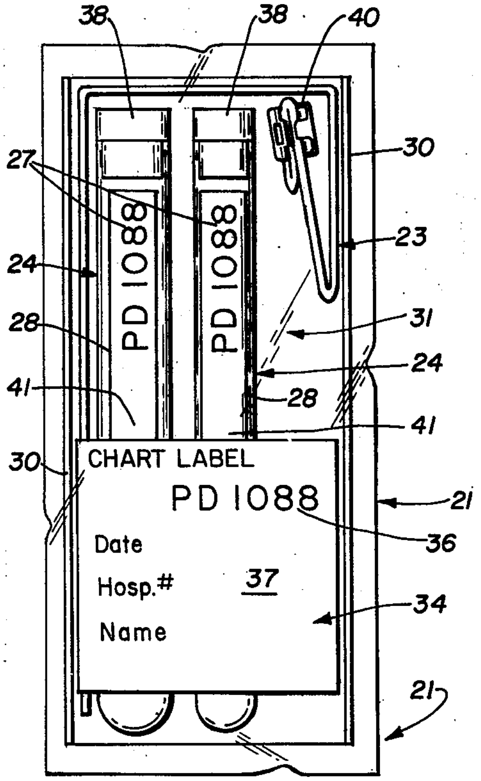
FIG. 1 is a front elevation view of a prepackaged patient identification kit.

Correlation of patients with their specimens, their records and therapeutic agents administered to them is accomplished in the method and apparatus of the present invention by providing a pre-packaged patient identification kit in which the key components necessary for taking specimens and identifying the patient and his records are provided in the kit with identical pre-numbered patient identifying indicia. Thus, the kit of the present invention includes wristband means 23, formed for secure attachment to the patient, usually at the wrist or ankle, and at least one specimen container means 24 formed for receipt of a specimen taken from the patient. Wristband means 23 and specimen container means 24 are all mounted in package means 21, and the wristband and specimen container are each provided with identical identifying indicia, namely, indicia 26 on wristband 23 (FIG. 2) and indicia 27 on container means 24. The patient identifying indicia 26 and 27 on the wristband and on the specimen container are affixed thereto in a tamper-resistant manner. For example, the indicia 26 on the wristband is mounted inside the plastic tube or envelope conventionally used for wristband means 23. Alternatively, a factory imprinted indicia can be provided on a wristband specially manufactured for the purpose. Additionally, the indicia 27 can be provided on a label 28, or the like, which is covered with a protective transparent coating (e.g., tape) or permanently affixed to specimen container 24. Alternatively, indicia 27 can even be formed in the container surface, such as by etching or the like.

The key advantage of the pre-packaged patient identification kit of FIG. 1 is that the sample receiving container means 24 and the wristband means 23 or both prenumbered with indicia that are identical and placed in a common package. This numbering takes place in the calm atmosphere of the manufacturer and subject to his quality control. Thus, all the physicians or other phlebotomist under emergency or routine conditions need do is remove the wristband from package 21, attach it to the patient, and take the specimen in container means 24 which accompanies the wristband. There is no need to peel off labels, fill in wristband information, and affix labels to specimen containers provided from another source. The physician does not build or otherwise create the system under the time pressure and tension of emergency or routine medical diagnosis and treatment.

Figure 2:
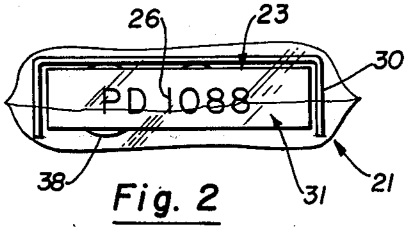
FIG. 2 is a top view of the kit in FIG. 1.
Figure 3:
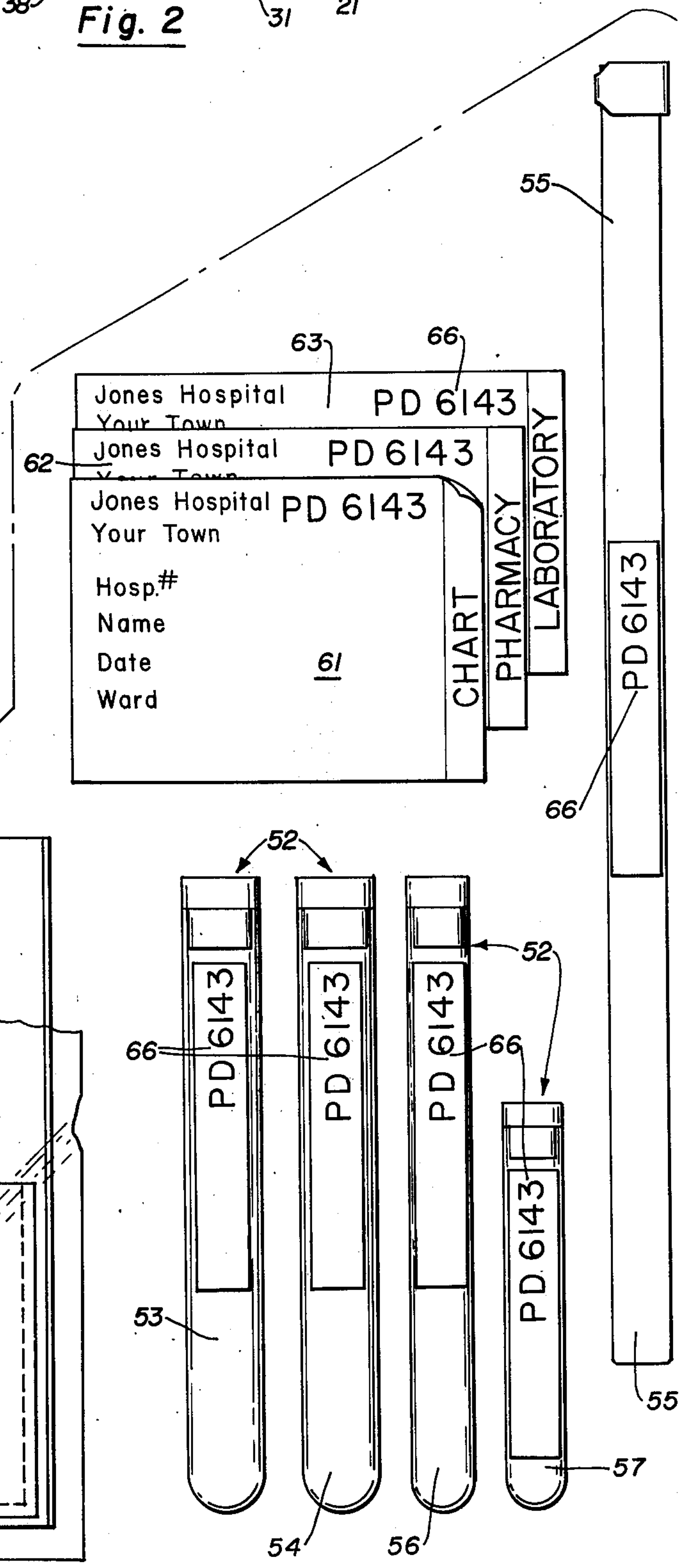
FIG. 3 is a front elevational view of an alternative embodiment showing the components of the kit removed.
Figure 3:
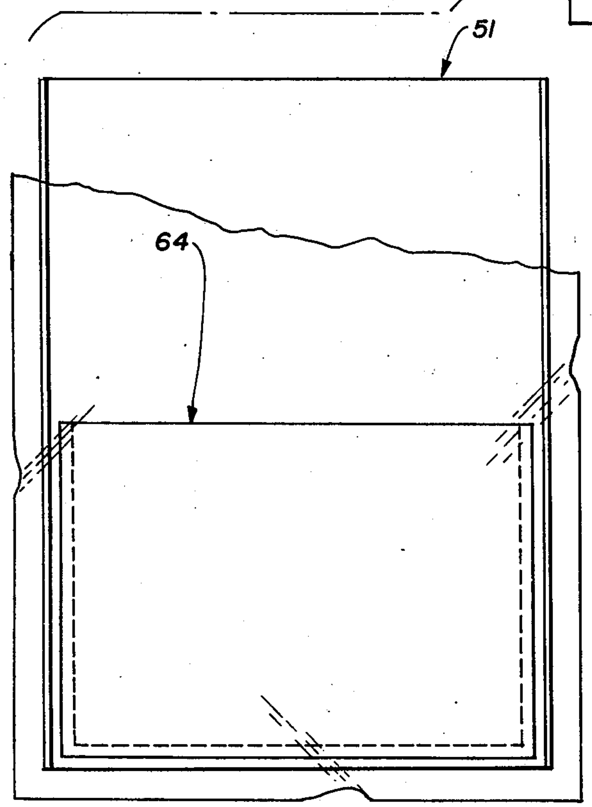

In order to insure the integrity of the kit of the present invention, it is preferable that package means 21 be formed with a transparent portion 31; in FIGS. 1, 2 and 3 the entire package means is transparent. The transparent portion enables visual verification of the identical nature of all of the patient identifying indicia 26 and 27. Thus, in addition to the quality control program at the manufacturer's plant where packaging of the kits occurs, the individual phlebotomist may verify the identical numbering of all of the components of the kit by viewing through transparent portion 31. As will be understood, as used herein, the expression "transparent portion" can include an opening or openings in an opaque package means or, alternatively, can include a package means 21 which is formed partially or entirely out of a transparent material, such as plastic. Wristband means 23 and specimen container means 24 are positioned so that indicia 26 and 27 face outwardly for viewing through transparent portion 31. In the kit of FIGS. 1 and 2 a U-shaped reinforcing card 30 is positioned inside package 21, and card 30 or the transparent plastic package 21 can be imprinted on the back side with a simple set of instructions for use of the kit.

In order to enable correlation of the records of the patient with the specimens and patient himself, it is further preferable to provide label means, generally designated 34, which is formed for attachment to a record of the patient and provided with patient identifying indicia 36 thereon. Indicia 36 is identical to indicia 26 and 27. Label means 34 is also preferably positioned in package means 21 in an orientation enabling visual verification of the identical nature of indicia 36 with that of the indicia 26 and 27. Label means 34 may be provided with an area 37 into which the hospital number, name, date and ward of the patient may be entered, and the label can be of the pressure-sensitive kind which can be peeled off a backing in a conventional manner and placed on a chart for the patient. While the information on label 34 is highly desirable, and even required by law in connection with transfusions, if this information is not accurately filled in, or even omitted in the press of emergency treatment, the specimen taken can still be correlated to a patient having a wristband and to a record corresponding to that patient, all by the identical indicia 26, 27 and 36. Moreover, it would also be possible for some of the information on label 34 to be previously inserted by a clerical assistant under non-emergency conditions if it is in an outside or auxilliary pocket as shown in the kit of FIG. 3. For example, each ward might have its own kits pre-identified by the ward name or number.

It is a further important feature of the present invention, in order to act as an effective reminder to the physicians and others using the system, that wristband means 23 be positioned in package means 21 with respect to the specimen container means 24 in a manner preventing use of the specimen container prior to handling of the wristband. Thus, one cannot get at containers 24 to collect a specimen without handling wristband 23, since it extends across the tops 38 through which the specimens must be introduced into the containers. It is further preferable that wristband 23 be detachably and safely secured to containers 24 so as to require conscious removal of the wristband in order to permit use of the containers. This can be accomplished, for example, by small sections of tape which detachably secure the wristband to the containers over tops 38. The phlebotomist can, therefore, remove the wristband and containers as a unit from package 21, and then detach the wristband from the containers, which will physically remind him to place the wristband on the patient's wrist or ankle before using the containers. Alternatively, the kit can be held in one hand and the wristband can be pulled out alone before the tubes. The wristband also may be folded into the wristband clamp 40 (FIG. 1) so the clamp will not have been closed in handling prior to use.

If the kit of the present invention is to be employed in connection with assuring patient-specimen correlation in connection with blood transfusions, the kit can be advantageously formed to include two specimen container tubes 24, which are advantageously evacuated blood collection tubes of the type commonly availble in the industry. For example, evacuated blood collection tubes are sold under the brand name VACUTAINER by Becton-Dickinson of Rutherford, New Jersey. Thus, tubes 24 can be evacuated blood collection tubes formed for receipt of a blood specimen. It is preferable that the kit include two evacuated blood collection tubes. One tube is used to take a specimen that can be centrifuged for blood serum studies and optionally a portion of this serum could be used for chemistry testing; the other (optional) tube being evacuated but also having an anticoagulant therein so that the specimen can be used for cell studies. A portion of the specimen in this tube could be used for hematology testing and special (as well as routine) blood bank studies. Such evacuated blood collection tubes conventionally also have tops or stoppers 38 which are color coded to indicate which tube contains the anticoagulant material and which does not. The convention presently employed in the industry is for one of stoppers 38 (the collection tube for serum studies) to be red while the other stopper (the tube having anticoagulant therein) is lavender or purple.

Again, each of the tubes includes patient identifying indicia 27 on labels 28, and tubes 24 also can include an auxilliary label or an area on a lower portion of each of indicia labels 28 to provide a data recording surface for the recording of the ward, date, name and hospital number of the patient on the specimen containers. Present statutes require the recording of this information by the physician or other phlebotomist who takes the blood specimen, but it is the correlation of indicia 27 with indicia 26 on wristband 23 that provides the separate and additional positive patient-specimen correlation. The addition of the name, ward, date and hospital number to the data recording surface of lower portion 41 of label 28 is essential for legal use of the present system, and the present system readily accommodates this statutory requirement by the provision of appropriate blank labels either on the inside of the kit or provided to the nursing station to be completed and attached to the outside of the kit before approaching the patient.

Use of the apparatus of FIGS. 1 and 2 in a typical blood transfusion application can now be described. The phlebotomist first confirms that all of the patient identifying indicia 26, 27 and 36 on wristband 23, tubes 24 and chart label 34 are identical by viewing the same through transparent package means 21. If any one of the four indicia vary, the entire package should be thrown out. If they are all identical, package 21 can be opened and the wristband and blood collection tubes removed as a unit. Wristband 23 then can be detached from the collection tubes 24 and attached to the wrist or ankle of the patient. The blood collection tubes can now be used by adding a needle holder and blood collection needle—a syringe may also be used—and the specimens taken in the usual manner. As each specimen is taken, the phlebotomist or physician writes in the name, ward and date on lower portion 41 of label 28 or on another data recording surface provided for tubes 24. Chart label 34 can be attached to the chart records of the patient, and the date, hospital number, ward and name of the patient can be filled in on area 37 of the chart label. Conventional blood requisition forms can also be filled in by the physician to indicate the number of units of blood, etc. which are required for the patient. The specimen tubes 24, together with the blood requisition forms, are then forwarded to the blood bank. At the blood bank the specimens are studied in the usual manner to type the blood and identify the appropriate antigens and their corresponding lack of antibodies for matching of the transfusion unit(s) to the specimen.

The blood bank is provided with a plurality of blank labels on which the technologist can fill in information such as the date, hospital number, ward, name of the patient and, most importantly, patient identifying indicia corresponding to the indicia on the specimen containers 24. The patient identifying indicia is also added to all appropriate permanent blood bank records by the technologist. This filling in of the indicia to be placed on the donor blood units at the blood bank is accomplished in the calm of the blood bank facility, rather than the pandemonium of an emergency room. Moreover, the labels which are provided to the blood bank are preferably not pre-numbered with the patient identifying indicia. If the blood bank labels were pre-numbered with the patient identifying indicia, they would preferably be placed in the kit and would have to accompany the specimen containers at all times. There is always the possibility that they could become lost or that such labels might become intermixed with other specimens, with resultant transfusion errors. In the system of the present invention it would admittedly be possible for the blood bank technologists to transpose numbers or improperly copy the identification indicia onto the labels made in the blood bank and to be placed upon the unit(s) of blood to be transfused, but the ultimate check is that the label on the unit of blood must have an identification indicia that is the same as on a wristband of the patient. A further check is provided by requiring the person calling for the blood unit to present appropriate indicia as well as patient name, etc., before blood is released for transfusion. Thus, while there is some chance for error in a system which requires filling in of the identification number at the blood bank, there is also a chance of error in a system in which additional labels are carried along with the specimen to be placed on the unit(s) of blood at the blood bank. It is believed, however, that technologists working with blank labels at the blood bank are less likely to transpose numbers and commit errors than are clerks and technologists working with systems which employ multiple labels that are handled both at the emergency room or on the wards and at the blood bank.

The last step in the use of the system is for the transfusionist, who receives the unit of blood from the blood bank with the label thereon having the patient identifying indicia copied onto the label, to check that indicia with indicia 26, as well as name and hospital number, on wristband 23 of the patient prior to giving the transfusion. If the indicia does not check, the transfusion should not be given, and the unit should be sent back to the blood bank to determine where the error has been made. Unless the indicia on the label on the unit of blood matches the wristband, there has, at some level, been a failure to correlate the specimen taken from the patient with the blood to be administered. If the indicia does match, the transfusionist knows that the specimen taken corresponded and can be correlated to the patient having wristband 23. Moreover, the blood bank has matched that specimen to the unit of blood having the same identifying number or indicia, and accordingly, that there is an extremely high assurance that the transfusion to be undertaken is free of clerical and administrative error.

Additionally, it might be noted that when a multiplicity of physicians and technologists are involved, the patient's record will have the identifying indicia which will indicate that a specimen was drawn for that patient and when the specimen was drawn. The record may also contain the comments of previous physicians, phlebotomists, etc. concerning the patient and his condition. These records can be consulted by a subsequent physician at the time of transfusion, again with a high assurance that the record being consulted corresponds to the patient being treated. This correlation of the records to the patient may be particularly important when the patient is in surgery and the wristband may not be readily visible in instances of a draped patient or if a particular procedure requires the cutting off of the wristband.

As will be appreciated, the system of the present invention can be employed to enable the dispensing of medicines and therapeutic agents other than blood, and to correlate the results of testing from other laboratory areas; and the kit if FIG. 3 includes four blood specimen receiving container means 52 for achievement of that purpose. All four containers 53, 54, 56 and 57 can be evacuated blood collection tubes. Tubes 53 and 54 can be used as described in connection with tubes 24 of the kit of FIG. 1, and containers 56 and 57 can be used for any or all of the many other types of laboratory testing of additional blood specimens. The selection of four evacuated blood specimen tubes for the kit of FIG. 3 is based upon the fact that almost all patients seen in emergency and/or admitted to a hospital have some blood analyses done, and these four types of tubes have the proper additives for blood collection appropriate for a number of tests essential for diagnosis and thus treatment by the physician. Testing of other specimens probably will also be done on a patient, but the clinical signs should preclude improper treatment of the patient based upon the test results, while clinical signs may not, and sometimes cannot, rule out improper treatment based on erroneous blood test results —transfusion error, diabetes, peritonitis, clotting abnormalities, etc. The manufacturer may provide, however, a different selection of tubes for the kit of the present invention.

Thus, the kit can be used to correlate a patient with his specimens, records, medicines and other therapy which might be administered to him throughout his stay in the hospital. For this purpose, the kit would advantageously include a multiplicity of labels, such as chart label 61, pharmacy label 62 and laboratory label 63. These labels can be conveniently stored in an auxiliary compartment or pocket 64, which can be advantageously placed on the front of package means 51. The auxiliary pocket portion 64 is also preferably transparent to enable viewing of patient identifying indicia 66 for confirmation of the identical nature of the same. Moreover, the pocket 64 is advantageously formed for selective removal of labels 61, 62 and 63 from the pocket, without the need of disturbing specimen containers 52 or wristband 55 positioned in the main portion of the package or kit.

The patient identification kit 51 can be used in the same manner as was described in connection with kit 21 for blood transfusions. The first step would be to remove labels 61, 62 and 63 from auxiliary pocket 64 and be certain that the patient identifying indicia 66 all correspond to the indicia 66 on collection tubes 52 and wristband 55. This could also advantageously be accomplished by forming the labels so that the patient identifying indicia 66 all can be viewed from the front of the package means 51 without removal from pocket 64. The provision of the labels in an auxiliary pocket, however, enables the physician or phlebotomist, after determining that all the indicia are identical, to hand the labels to a clerk or nurse who will affix the same on the corresponding patient records. The physician or phlebotomist can then immediately place the wristband 55 on the patient's wrist or ankle and proceed with taking specimens, etc. The specimens, orders for medicine, orders for other therapy or agents will then be conducted in the usual manner with the usual documentation employed by the hospital, with the exception that separate and additional patient identifying indicia 66 will be entered into the hospital documentation and onto labels on any therapeutic or diagnostic agents dispensed from the pharmacy, laboratory or other source within the hospital. The administering physician or nurse can, therefore, inspect the label on the therapeutic or diagnostic agent for patient identifying indicia 66 and compare the same wristband 55 on the patient before allowing a therapeutic agent to be adminstered. The clerk or nurse can inspect laboratory reports for patient identifying indicia before chart insertion. Patient identifying indicia 66 on wristband 55 can be added to labels of specimens taken for subsequent laboratory tests.

Accordingly, the patient identification kit and method of the present invention enables a correlation of the patient with his specimens and records to thereby insure proper treatment of patients. The effectiveness of the identification kit and method is the result of prenumbering of wristbands and specimen containers, and optionally chart labels; and placing the same in a common kit. Thus, the system simply can be used —not constructed, built-up or created by the physician or supportive personnel acting as phlebotomist.

What is claimed is:

1. A pre-packaged patient identification kit for use in assuring correlation between a patient and his specimens during patient treatment comprising:
  package means;
  wristband means formed for secure attachment to a patient, said wristband means being provided with patient identification indicia previously affixed thereto in a tamper-resistant manner;
  at least one specimen container means formed for receipt of a specimen taken from said patient, said specimen container means being provided with patient identification indicia previously affixed thereto in a tamper-resistant manner; and
  each said patient identifying indicia being identical, and said wristband means and said specimen container means being removably positioned in said package means.

2. A pre-packaged patient identification kit as defined in claim 1, and
  label means formed for attachment to a record of said patient and provided with patient identifying indicia identical to said indicia on said wristband means and said specimen container means;
  said package means is formed to be readily carried by hand and is formed with a transparent portion; and
  said wristband means, said specimen container means and said label means are positioned in said package means in an orientation enabling visual verification of the identical nature of each of said patient identifying indicia through said transparent portion.

3. A pre-packaged patient identification kit as defined in claim 1 wherein,
  said wristband means is positioned in said package means with respect to said speciment container means in a manner preventing use of said specimen container means prior to handling of said wristband means.

4. A pre-packaged patient identification kit as defined in claim 3 wherein,
  said wristband means is detachably secured to said specimen container means in a manner requiring removal of said wristband means in order to permit use of said specimen container means.

5. A pre-packaged patient identification kit as defined in claim 1 wherein,
  said kit includes a plurality of specimen container means each formed with identical patient identifying indicia affixed thereto in a tamper-resistant manner.

6. A pre-packaged identification kit as defined in claim 1 wherein,
  said specimen container means is formed for receipt of a blood specimen.

7. A pre-packaged patient identification kit as defined in claim 6 wherein,
  said specimen container means is an evacuated blood collection tube.

8. A pre-packaged patient identification kit as defined in claim 1 wherein,
  said kit includes a plurality of label means each formed with identical patient identifying indicia.

9. A pre-packaged patient identification kit as defined in claim 8 wherein,
  said package means is formed with an auxiliary pocket portion, said label means are removably positioned in said pocket portion, and said pocket portion is formed for access to and selective removal of said label means therefrom without removal of any other component from said package means.

10. A pre-packaged patient identification kit as defined in claim 1 wherein,
  said specimen container means includes four specimen collection tubes with at least two of said tubes being evacuated blood collection tubes and each of said tubes having identical patient identifying indicia thereon;
  label means including at least three labels including a chart label, a pharmacy label and a laboratory label and each of said labels contains patient identifying indicia identical to each other and to said indicia on said tubes; and
  said package means is formed with a main storage portion with said tubes and said wristband positioned therein, and is formed with an auxiliary pocket portion with said labels positioned in said pocket portion.

11. A pre-packaged patient identification kit as defined in claim 1 wherein,
  said specimen container means includes a first evacuated blood collection tube formed for receipt of a blood specimen for serum studies and a second evacuated blood collection tube having anticoagulent therein and formed for receipt of a blood specimen for cell studies, with each of said tubes being provided with identical patient identifying indicia, said tubes each further being provided with a data recording surface for recording of data thereon relative to the blood specimens;
  label means in the form of a chart label;
  said wristband means passes over the top of each of said tubes formed for introduction of the samples into said tubes, and said wristband means is releasably secured over said top to inhibit use of said tubes without removal of said wristband means; and
  said package means is formed with a transparent portion, and said wristband means, said tubes and said chart label being positioned inside said package means with said patient identifying indicia visible to the exterior of said package means while said package means is in a closed condition.

* * * * *